United States Patent [19]

Beschke et al.

[11] 4,163,854
[45] Aug. 7, 1979

[54] PROCESS FOR THE PRODUCTION OF 3-METHYL PYRIDINE

[75] Inventors: Helmut Beschke; Heinz Friedrich, both of Hanau, Fed. Rep. of Germany

[73] Assignee: Deutsche Gold- und Silber Scheideanstalt vormals Roessler, Frankfurt, Fed. Rep. of Germany

[21] Appl. No.: 871,979

[22] Filed: Jan. 24, 1978

[30] Foreign Application Priority Data

Jan. 26, 1977 [DE] Fed. Rep. of Germany ....... 2703070

[51] Int. Cl.$^2$ .......................................... C07D 213/12
[52] U.S. Cl. .................................................. 546/251
[58] Field of Search ...................................... 260/290 P

[56] References Cited

U.S. PATENT DOCUMENTS 3,898,177  8/1975  Beschke et al. ...................... 252/432
3,917,542  11/1975  Beschke et al. ................... 260/290 P
3,960,766  6/1976  Beschke et al. ....................... 252/437

FOREIGN PATENT DOCUMENTS 1273826  9/1961  France ................................. 260/290 P

OTHER PUBLICATIONS

Emmett, Catalysis, vol. VII, Reinhold Pub. Co., pp. 5–9 (1960).

*Primary Examiner*—Alan L. Rotman
*Attorney, Agent, or Firm*—Cushman, Darby & Cushman

[57] ABSTRACT

3-Methyl pyridine is produced by the catalytic reaction of acrolein and propionaldehyde with ammonia in the gas phase. There is used as the catalyst a highly dispersed aluminum silicate containing 3 to 30 weight percent aluminum oxide, a BET surface area of 200 to 800 m$^2$/g, a pore volume of 0.4 to 1.0 cm$^3$/g and a pore diameter of 20 to 100×10$^{-8}$ cm.

19 Claims, No Drawings

PROCESS FOR THE PRODUCTION OF 3-METHYL PYRIDINE

BACKGROUND OF THE INVENTION

The invention is directed to a process for the production of 3-methyl pyridine by catalytic reaction of acrolein and propionaldehyde with ammonia in the gas phase.

It is known that in the reaction of acrolein with ammonia in the gas phase in the presence of catalysts 3-methyl pyridine is formed. As catalysts there have been especially used compounds of the elements Al, F and O which additionally contain at least one element of the second, third or fourth groups of the periodic system and which have been treated with oxygen at temperatures of 550° to 1200° C. (German Offenlegungsschrift No. 2,151,417 or corresponding Beschke U.S. Pat. No. 3,898,177) or at least two elements of the second, fourth, fifth or sixth groups of the periodic system (German OS No. 2,224,160 or corresponding Beschke U.S. Pat. No. 3,960,766), or at least one element of the second main group of the periodic system (German OS No. 2,239,801 or corresponding Beschke U.S. Pat. No. 3,917,542. It is also known to carry out the reaction in a fluidized bed with the acrolein fed in separately from the ammonia (German OS No. 2,449,340 and corresponding Beschke U.S. Pat. application No. 622,488 filed Oct. 15, 1975). The disadvantage of these processes is that besides 3-methyl pyridine there is also formed to a considerable extent pyridine and the yield of 3-methyl pyridine is below 50%.

Furthermore, it is known to produce 3-methyl pyridine by reacting a mixture of acrolein and propionaldehyde with ammonia. As catalysts there are used aluminum oxide, silica or silica in admixture with 5 to 50% of aluminum oxide, in a given case with the addition of oxides of additional elements (French Pat. No. 1,273,826). In this process the yield of 3-methyl pyridine in the best case is 53% (Example 29).

SUMMARY OF THE INVENTION

There has now been found a process for the production of 3-methyl pyridine by catalytic reaction of acrolein and propionaldehyde with ammonia in the gas phase which is characterized by using as the catalyst highly dispersed aluminum silicate which contains 3 to 30 weight percent aluminum oxide, a BET surface area of 200 to 800 m$^2$/g, a pore volume of 0.4 to 1.0 cm$^3$/g and a pore diameter of 20 to 100×10$^{-8}$ cm (20 to 100 Å). With this process there is produced considerably higher yields of 3-methyl pyridine than in the known processes.

The aluminum silicates used according to the invention preferably have an aluminum oxide content of 5 to 20% and especially from 10 to 15%. They preferably have a BET surface area of 300 to 600 m$^2$/g, a pore volume of 0.6 to 0.8 cm$^3$/g, a pore volume of 0.6 to 0.8 cm$^3$/g and a pore diameter of 40 to 80×10$^{-8}$ cm.

The aluminum silicates can be made in known manner, for example, by treating an aqueous sodium silicate solution with sulfuric acid and mixing the silica gel produced with aluminum sulfate and ammonia, separating and freeing of the aluminum silicate from foreign ions, drying and tempering (Paul H. Emmett, Catalysis, Vol. VII, Reinhold Publishing Corp., especially pages 5 to 9). The entire disclosure of Emmett is hereby incorporated by reference and relied upon.

To carry out the process of the invention acrolein, propionaldehyde and ammonia are added in customary manner in gaseous form. The molar proportions can be chosen substantially at random. However, it is generally suitable per mole of acrolein to use about 0.1 to 1.0 mole, preferably 0.2 to 0.8 mole, particularly 0.4 to 0.6 mole of propionaldehyde. Besides it is generally suitable to add per mole of aldehyde (acrolein and propionaldehyde) at least about 1 mole of ammonia. It is advantageous to use per mole of aldehyde about 1.0 to 3.0 moles, especially 1.3 to 2.5 moles, of ammonia. Suitable there is introduced additionally an inert gas, especially nitrogen, that is, advantageously per mole of aldehyde 0.5 to 3.0 moles, particularly 1.0 to 2.5 moles, of inert gas.

The catalyst is used in a fixed bed, generally in a particle size of 0.2 to 3.0 mm, especially of 0.5 to 2.0 mm, or preferably in a fluidized bed, generally in a particle size of 0.1 to 3.0 mm, especially of 0.2 to 2.0 mm. Advantageously the aldehydes are fed into the reaction space separately from the ammonia. Particularly, there is chosen for this purpose the procedure of German OS No. 2,449,340 or corresponding Beschke U.S. Pat. application No. 622,488 filed Oct. 15, 1975, however, with the difference that instead of acrolein in each case there is added a mixture of acrolein and propionaldehyde. There are hereby incorporated by reference and relied upon the entire disclosures of German OS No. 2,449,340 and Beschke U.S. Pat. application No. 622,488.

The reaction takes place at temperatures between about 300° and 500° C., especially between 380° and 480° C. The pressure can be chosen substantially at random, however, it is recommended so that a simple apparatus can be used to operate at normal pressure or only moderately lowered or elevated pressure up to about 3 bar. A slight under pressure or over pressure results in a given case in that the gases are sucked through the plant or forced through by pressure.

The process can comprise, consist essentially of or consist of the steps set forth and the materials employed can comprise, consist essentially of or consist of those set forth.

Unless otherwise indicated all parts and percentages are by weight.

DESCRIPTION OF THE PREFERRED EMBODIMENT

Example 1

There was used a fluidized bed reactor. This consisted of a tube 70 mm wide which had a free space in its lower portion 200 mm high; thereover at intervals of 50 mm there were 40 wire screens each having an interval between meshes of 5 mm and there was provided above a free space having a height of 600 mm and a width of up to 160 mm.

There were led into the reactor in gaseous form in uniform flow hourly from below a gas mixture of 1875 normal liters (i.e., measured at standard temperature and pressure) of nitrogen and 2690 normal liters of ammonia and from the side there were led into the fluidized bed 130 mm above the bottom of the reactor a gaseous mixture of 2244 grams of acrolein, 1162 grams of propionaldehyde and 260 normal liters of nitrogen.

The reactor contained 2.0 kg of catalyst. The catalyst consisted of aluminum silicate containing 13% $Al_2O_3$, had a BET surface area of 500 $m^2/g$, a pore volume of 0.75 $cm^3/g$, a pore diameter of $60 \times 10^{-8}$ cm (i.e., 60 Å) and a particle size of 0.4 to 1.0 mm.

The temperature in the reactor was held at 440° C. The reaction mixture which left the reactor was free from acrolein and propionaldehyde. It was led at a temperature of 250° C. into a gas washing apparatus in which the 3-methyl pyridine and pyridine formed were washed out by means of water. The remaining residual gas of ammonia and nitrogen after addition of 940 normal liters of ammonia hourly were recycled into the reactor.

The reaction of acrolein and propionaldehyde was 100%. There were recovered hourly 1693 grams of 3-methyl pyridine, corresponding to a yield of 60.6% based on the aldehydes added. Besides there were obtained 147 grams of pyridine, corresponding to a yield of 6.2%. Per kg of catalyst per hour there was a yield of 3-methyl pyridine of 846 grams.

Example 2

The procedure was the same as in Example 1 but there was fed in hourly 2690 grams of acrolein and 700 grams of propionaldehyde. The yield of 3-methyl pyridine was 1643 grams, corresponding to 58.8%, the yield of pyridine 240 grams, corresponding to 10.1%. Per kg of catalyst per hour the yield of 3-methyl pyridine was 822 grams.

Example 3

The procedure was the same as in Example 1 but there were fed in hourly 1685 grams of acrolein and 1160 grams of propionaldehyde and the reaction was carried out at 460° C. The yield of 3-methyl pyridine was 1679 grams, corresponding to 60.1%, the yield of pyridine 171 grams, corresponding to 7.2%. Per kg of catalyst per hour the yield of 3-methyl pyridine was 840 grams.

What is claimed is:

1. In a process for the production of 3-methyl pyridine by the catalytic reaction of acrolein and propionaldehyde with ammonia in the gas phase the improvement comprising employing as the catalyst a highly dispersed aluminum silicate containing 3 to 30 weight percent aluminum oxide, a BET surface area of 200 to 800 $m^2/g$, a pore volume of 0.4 to 1.0 $cm^3/g$ and a pore diameter of 20 to $100 \times 10^{-8}$ cm and wherein the catalyst is employed in a fluidized bed and the acrolein and propionaldehyde are introduced into the reactor separately from the ammonia.

2. A process according to claim 1 wherein the catalyst has an aluminum oxide content of 5 to 20 weight percent, a BET surface area of 300 to 600 $m^2/g$, a pore volume of 0.6 to 0.8 $cm^3/g$ and a pore diameter of 40 to $80 \times 10^{-8}$ cm.

3. A process according to claim 2 wherein the aluminum oxide content is 10 to 15 weight percent.

4. A process according to claim 3 wherein per mole of acrolein there is employed 0.4 to 0.6 mole of propionaldehyde and per mole of total aldehyde 1.3 to 2.5 moles of ammonia.

5. A process according to claim 4 wherein there is also employed 1.0 to 2.5 moles of inert gas per mole of total aldehyde.

6. A process according to claim 2 wherein per mole of acrolein there is employed 0.4 to 0.6 mole of propionaldehyde and per mole of total aldehyde 1.3 to 2.5 moles of ammonia.

7. A process according to claim 6 wherein there is also employed 1.0 to 2.5 moles of inert gas per mole of total aldehyde.

8. A process according to claim 2 wherein per mole of acrolein there is employed 0.2 to 0.8 mole of propionaldehyde and per mole of total aldehyde 1.0 to 3.0 moles of ammonia.

9. A process according to claim 8 wherein there is also employed 0.5 to 3.0 moles of inert gas per mole of total aldehyde.

10. A process according to claim 1 wherein there is employed per mole of acrolein 0.4 to 0.6 mole of propionaldehyde.

11. A process according to claim 10 wherein there is employed per mole of total aldehyde 1.3 to 2.5 moles of ammonia.

12. A process according to claim 11 wherein there is also employed 1.0 to 2.5 moles of inert gas per mole of total aldehyde.

13. A process according to claim 1 wherein there is employed per mole of acrolein 0.2 to 0.8 mole of propionaldehyde and per mole of total aldehyde 1.0 to 3.0 moles of ammonia.

14. A process according to claim 13 wherein there is also employed 0.5 to 3.0 moles of inert gas per mole of total aldehyde.

15. A process according to claim 1 wherein there is employed per mole of acrolein 0.1 to 1.0 mole of propionaldehyde and at least 1 mole of ammonia per mole of total aldehyde.

16. A process according to claim 1 wherein the catalyst has a particle size of 0.1 to 3.0 mm.

17. A process according to claim 16 wherein the catalyst has a particle size of 0.2 to 2.0 mm.

18. A process according to claim 1 wherein the catalyst consists of said aluminum silicate.

19. A process according to claim 1 wherein the catalyst consists essentially of said aluminum silicate.

* * * * *